United States Patent
Einarsson

(10) Patent No.: US 11,717,283 B2
(45) Date of Patent: Aug. 8, 2023

(54) SUTURING DEVICE FOR LAPAROSCOPIC PROCEDURES

(71) Applicant: The Brigham And Women's Hospital, Inc., Boston, MA (US)

(72) Inventor: Jon Einarsson, Boston, MA (US)

(73) Assignee: The Brigham and Women's Hospital, Inc., Boston, MA (US)

(*) Notice: Subject to any disclaimer, the term of this patent is extended or adjusted under 35 U.S.C. 154(b) by 54 days.

(21) Appl. No.: 16/938,205

(22) Filed: Jul. 24, 2020

(65) Prior Publication Data

US 2020/0352559 A1 Nov. 12, 2020

Related U.S. Application Data

(63) Continuation of application No. 15/987,733, filed on May 23, 2018, now Pat. No. 10,799,233, which is a
(Continued)

(51) Int. Cl.
*A61B 17/04* (2006.01)
*A61B 17/062* (2006.01)
(Continued)

(52) U.S. Cl.
CPC ...... *A61B 17/0469* (2013.01); *A61B 17/0482* (2013.01); *A61B 17/0491* (2013.01);
(Continued)

(58) Field of Classification Search
CPC ............ A61B 17/0469; A61B 17/0482; A61B 17/0491; A61B 17/0625;
(Continued)

(56) References Cited

U.S. PATENT DOCUMENTS

| 1,327,577 A | 1/1920 | Turner |
| 1,822,330 A | 9/1931 | Ainslie |

(Continued)

FOREIGN PATENT DOCUMENTS

| EP | 1839592 A1 | 10/2007 |
| WO | 0134035 A1 | 5/2001 |

(Continued)

OTHER PUBLICATIONS

WIPO. International Preliminary Report on Patentability for International Application No. PCT/US2014/058638 (Kia, Michael A. et al.) dated Apr. 14, 2016, 9 pages.
(Continued)

*Primary Examiner* — Mohamed G Gabr
(74) *Attorney, Agent, or Firm* — DeWitt LLP

(57) ABSTRACT

A suturing device includes an elongated body having an outer wall defining an interior space of the body, a shaft located in the interior space, and a needle mounted on a distal end of the shaft. The needle has a distal section transverse to a longitudinal axis of the shaft. The distal section of the needle terminates in a first jaw and a second jaw forming a forceps defining a piercing tip. The first jaw and second jaw have a grasping position wherein the first jaw and second jaw grasp a suturing material, and a release position wherein the first jaw and second jaw release the suturing material. After grasping the suturing material with the needle, the shaft rotates the needle to advance the needle (Continued)

and suturing material through tissue and mesh placed on the tissue. Spaced apart portions of the suturing material are then fused to create a suture.

16 Claims, 7 Drawing Sheets

Related U.S. Application Data continuation of application No. 14/397,682, filed as application No. PCT/US2013/038746 on Apr. 30, 2013, now abandoned.

(60) Provisional application No. 61/641,069, filed on May 1, 2012.

(51) Int. Cl.
*A61B 17/00* (2006.01)
*A61B 17/06* (2006.01)

(52) U.S. Cl.
CPC ............... *A61B 17/0625* (2013.01); *A61B 2017/00805* (2013.01); *A61B 2017/0619* (2013.01); *A61B 2017/06042* (2013.01)

(58) Field of Classification Search
CPC ........... A61B 2017/00805; A61B 2017/06042; A61B 2017/0619
See application file for complete search history.

(56) References Cited

U.S. PATENT DOCUMENTS

| | | |
|---|---|---|
| 2,327,353 A | 8/1943 | Karle |
| 2,601,564 A | 6/1952 | Smith |
| 3,197,997 A | 8/1965 | Kurtz |
| 3,311,110 A | 3/1967 | Singerman et al. |
| 3,344,790 A | 10/1967 | Dorner |
| 3,762,418 A | 10/1973 | Wasson |
| 3,834,599 A | 9/1974 | Herr |
| 3,835,912 A | 9/1974 | Kristensen et al. |
| 3,910,282 A | 10/1975 | Messer et al. |
| 3,951,261 A | 4/1976 | Mandel et al. |
| 3,972,418 A | 8/1976 | Schuler et al. |
| 4,027,608 A | 6/1977 | Arbuckle |
| 4,074,732 A | 2/1978 | Wilkens |
| 4,235,177 A | 11/1980 | Arbuckle |
| 4,327,655 A | 5/1982 | Addy et al. |
| 4,331,277 A | 5/1982 | Green |
| 4,437,465 A | 3/1984 | Nomoto et al. |
| 4,440,171 A | 4/1984 | Nomoto et al. |
| 4,509,945 A | 4/1985 | Kramann et al. |
| 4,527,564 A | 7/1985 | Eguchi et al. |
| 4,557,265 A | 12/1985 | Andersson |
| 4,621,640 A | 11/1986 | Mulhollan et al. |
| 4,841,888 A | 6/1989 | Mills et al. |
| 4,899,746 A | 2/1990 | Brunk |
| 4,957,502 A | 9/1990 | Takase |
| 5,080,663 A | 1/1992 | Mills et al. |
| 5,089,012 A | 2/1992 | Prou |
| 5,174,300 A | 12/1992 | Bales |
| 5,201,760 A | 4/1993 | West |
| 5,210,376 A | 5/1993 | Caviar |
| 5,269,806 A | 12/1993 | Sardelis et al. |
| 5,305,281 A | 4/1994 | Lubeck |
| 5,306,281 A | 4/1994 | Beurrier |
| 5,308,353 A | 5/1994 | Beurrier |
| 5,318,566 A | 6/1994 | Miller |
| 5,318,578 A | 6/1994 | Hasson |
| 5,330,502 A | 7/1994 | Hassler |
| 5,344,061 A | 9/1994 | Crainich |
| 5,358,498 A | 10/1994 | Shave |
| 5,364,408 A | 11/1994 | Gordon |
| 5,373,101 A | 12/1994 | Barabolak |
| 5,376,101 A | 12/1994 | Green et al. |
| 5,383,883 A | 1/1995 | Wilk et al. |
| 5,387,221 A | 2/1995 | Bisgaard |
| 5,403,344 A | 4/1995 | Allen |
| 5,417,700 A * | 5/1995 | Egan ............... A61B 17/12013 606/228 |
| 5,437,681 A | 8/1995 | Meade et al. |
| 5,454,819 A | 10/1995 | Knoepfler |
| 5,462,558 A | 10/1995 | Kolesa et al. |
| 5,472,081 A | 12/1995 | Kilgrow et al. |
| 5,474,568 A | 12/1995 | Scott |
| 5,478,344 A | 12/1995 | Stone et al. |
| 5,478,345 A | 12/1995 | Stone et al. |
| 5,480,409 A | 1/1996 | Riza |
| 5,503,266 A | 4/1996 | Kalbfeld et al. |
| 5,514,159 A | 5/1996 | Matula et al. |
| 5,540,705 A | 7/1996 | Meade et al. |
| 5,571,119 A | 11/1996 | Atala |
| 5,575,800 A | 11/1996 | Gordon |
| 5,578,044 A | 11/1996 | Gordon et al. |
| 5,643,295 A | 7/1997 | Yoon |
| 5,645,552 A | 7/1997 | Sherts |
| 5,653,718 A | 8/1997 | Yoon |
| 5,665,096 A | 9/1997 | Yoon |
| 5,665,109 A | 9/1997 | Yoon |
| 5,669,490 A | 9/1997 | Colligan et al. |
| 5,675,961 A | 10/1997 | Cerwin et al. |
| 5,709,693 A | 1/1998 | Taylor |
| 5,713,910 A | 2/1998 | Gordon et al. |
| 5,715,942 A | 2/1998 | Li et al. |
| 5,741,277 A | 4/1998 | Gordon et al. |
| 5,755,729 A | 5/1998 | de la Torre et al. |
| 5,759,188 A | 6/1998 | Yoon |
| 5,766,186 A | 6/1998 | Faraz et al. |
| 5,814,069 A | 9/1998 | Schulze et al. |
| 5,814,071 A | 9/1998 | McDevitt et al. |
| 5,830,234 A | 11/1998 | Wojciechowicz et al. |
| 5,833,695 A | 11/1998 | Yoon |
| 5,860,992 A | 1/1999 | Daniel et al. |
| 5,891,160 A | 4/1999 | Williamson, IV et al. |
| 5,893,880 A | 4/1999 | Egan et al. |
| 5,906,273 A | 5/1999 | Pohle et al. |
| 5,908,426 A | 6/1999 | Pierce |
| 5,908,428 A | 6/1999 | Scirica et al. |
| 5,911,727 A | 6/1999 | Taylor |
| 5,941,901 A | 8/1999 | Egan |
| 5,954,733 A | 9/1999 | Yoon |
| 5,964,765 A | 10/1999 | Fenton, Jr. et al. |
| 5,968,077 A | 10/1999 | Wojciechowicz et al. |
| 5,993,466 A | 11/1999 | Yoon |
| 6,016,905 A | 1/2000 | Gemma et al. |
| 6,036,694 A | 3/2000 | Goble et al. |
| 6,048,351 A | 4/2000 | Gordon et al. |
| 6,053,908 A | 4/2000 | Crainich et al. |
| 6,056,751 A | 5/2000 | Fenton, Jr. |
| 6,056,771 A | 5/2000 | Proto |
| 6,059,827 A | 5/2000 | Fenton, Jr. |
| 6,071,289 A | 6/2000 | Stefanchik et al. |
| 6,096,051 A | 8/2000 | Kortenbach et al. |
| 6,106,545 A | 8/2000 | Egan |
| 6,126,666 A | 10/2000 | Trapp et al. |
| 6,135,385 A | 10/2000 | Martinez de Lahidalga |
| 6,136,010 A | 10/2000 | Modesitt et al. |
| 6,159,224 A | 12/2000 | Yoon |
| 6,174,324 B1 | 1/2001 | Egan et al. |
| 6,217,591 B1 | 4/2001 | Egan et al. |
| 6,261,307 B1 | 7/2001 | Yoon et al. |
| 6,270,508 B1 | 8/2001 | Klieman et al. |
| 6,286,746 B1 | 9/2001 | Egan et al. |
| 6,322,581 B1 | 11/2001 | Fukuda et al. |
| 6,332,888 B1 | 12/2001 | Levy et al. |
| 6,346,111 B1 | 2/2002 | Gordon et al. |
| 6,358,271 B1 | 3/2002 | Egan et al. |
| 6,409,743 B1 | 6/2002 | Fenton, Jr. |
| 6,423,088 B1 | 7/2002 | Fenton, Jr. |
| 6,443,962 B1 | 9/2002 | Gaber |
| 6,454,777 B1 | 9/2002 | Green |
| 6,454,778 B2 | 9/2002 | Kortenbach |
| 6,488,196 B1 | 12/2002 | Fenton, Jr. |

(56) References Cited

U.S. PATENT DOCUMENTS

| | | |
|---|---|---|
| 6,494,888 B1 | 12/2002 | Laufer et al. |
| 6,506,196 B1 | 1/2003 | Laufer |
| 6,558,400 B2 | 5/2003 | Deem et al. |
| 6,610,080 B2 | 8/2003 | Morgan |
| 6,656,194 B1 | 12/2003 | Gannoe et al. |
| 6,663,639 B1 | 12/2003 | Laufer et al. |
| 6,666,877 B2 | 12/2003 | Morgan et al. |
| 6,669,705 B2 | 12/2003 | Westhaver et al. |
| 6,719,763 B2 | 4/2004 | Chung et al. |
| 6,719,764 B1 | 4/2004 | Gellman et al. |
| 6,722,552 B2 | 4/2004 | Fenton, Jr. |
| 6,746,460 B2 | 6/2004 | Gannoe et al. |
| 6,755,843 B2 | 6/2004 | Chung et al. |
| 6,786,913 B1 | 9/2004 | Sancoff et al. |
| 6,835,200 B2 | 12/2004 | Laufer et al. |
| 6,877,352 B1 | 4/2005 | Schlereth |
| 6,893,434 B2 | 5/2005 | Fenton et al. |
| 6,908,427 B2 | 6/2005 | Fleener et al. |
| 6,923,819 B2 | 8/2005 | Meade et al. |
| 6,923,824 B2 | 8/2005 | Morgan et al. |
| 6,955,643 B2 | 10/2005 | Gellman et al. |
| 7,004,951 B2 | 2/2006 | Gibbens, III |
| 7,033,370 B2 | 4/2006 | Gordon et al. |
| 7,041,111 B2 | 5/2006 | Chu |
| 7,090,111 B2 | 8/2006 | Egan et al. |
| 7,131,980 B1 | 11/2006 | Field et al. |
| 7,144,401 B2 | 12/2006 | Yamamoto et al. |
| 7,166,116 B2 | 1/2007 | Lizardi et al. |
| 7,338,504 B2 | 3/2008 | Gibbens et al. |
| 7,615,060 B2 | 11/2009 | Stokes et al. |
| 7,628,796 B2 | 12/2009 | Shelton, IV et al. |
| 7,637,909 B2 | 12/2009 | Lechot et al. |
| 7,758,614 B2 | 7/2010 | Fenton et al. |
| 7,766,925 B2 | 8/2010 | Stokes et al. |
| 7,828,812 B2 | 11/2010 | Stokes et al. |
| 7,833,236 B2 | 11/2010 | Stokes et al. |
| 7,846,169 B2 | 12/2010 | Shelton, IV et al. |
| 7,862,572 B2 | 1/2011 | Meade et al. |
| 7,887,554 B2 | 2/2011 | Stokes et al. |
| 7,976,533 B2 | 7/2011 | Larsson |
| 7,976,555 B2 | 7/2011 | Meade et al. |
| 7,993,354 B1 | 8/2011 | Brecher et al. |
| 8,029,536 B2 | 10/2011 | Sorensen et al. |
| 8,066,737 B2 | 11/2011 | Meade et al. |
| 8,123,764 B2 | 2/2012 | Meade et al. |
| 8,197,508 B2 | 6/2012 | Egan et al. |
| 8,292,902 B2 | 10/2012 | Fenton |
| 8,469,973 B2 | 6/2013 | Meade et al. |
| 8,500,756 B2 | 8/2013 | Papa et al. |
| 8,623,048 B2 | 1/2014 | Brecher et al. |
| 8,641,728 B2 | 2/2014 | Stokes et al. |
| 8,702,732 B2 | 4/2014 | Woodard, Jr. et al. |
| 8,906,043 B2 | 12/2014 | Woodard, Jr. et al. |
| 9,017,346 B2 | 4/2015 | Kia et al. |
| 9,125,645 B1 | 9/2015 | Martin et al. |
| 9,173,655 B2 | 11/2015 | Martin |
| 9,220,496 B2 | 12/2015 | Martin et al. |
| 9,357,998 B2 | 6/2016 | Martin et al. |
| 9,370,354 B1 | 6/2016 | Martin et al. |
| 9,375,212 B2 | 6/2016 | Martin et al. |
| 9,398,905 B2 | 7/2016 | Martin |
| 9,427,226 B2 | 8/2016 | Martin et al. |
| 9,427,227 B2 | 8/2016 | Martin et al. |
| 9,445,807 B2 | 9/2016 | Brecher et al. |
| 9,451,948 B2 | 9/2016 | Meade et al. |
| 9,474,522 B2 | 10/2016 | Deck et al. |
| 9,474,523 B2 | 10/2016 | Meade et al. |
| 9,486,209 B2 | 11/2016 | Martin et al. |
| 9,498,207 B2 | 11/2016 | Martin et al. |
| 9,526,495 B2 | 12/2016 | Martin et al. |
| 10,799,233 B2 * | 10/2020 | Einarsson .......... A61B 17/0482 |
| 2001/0056283 A1 | 12/2001 | Carter et al. |
| 2002/0011508 A1 | 1/2002 | Egan et al. |
| 2002/0035371 A1 | 3/2002 | Westhaver et al. |
| 2002/0107530 A1 | 8/2002 | Sauer et al. |
| 2002/0116010 A1 | 8/2002 | Chung et al. |
| 2002/0116011 A1 | 8/2002 | Chee Chung et al. |
| 2002/0147456 A1 | 10/2002 | Diduch et al. |
| 2002/0173800 A1 | 11/2002 | Dreyfuss et al. |
| 2002/0188304 A1 | 12/2002 | Mollenauer et al. |
| 2002/0193809 A1 | 12/2002 | Meade et al. |
| 2002/0198542 A1 | 12/2002 | Yamamoto et al. |
| 2003/0083674 A1 | 5/2003 | Gibbens |
| 2003/0105475 A1 | 6/2003 | Sancoff et al. |
| 2003/0171760 A1 | 9/2003 | Gambale |
| 2003/0181924 A1 | 9/2003 | Yamamoto et al. |
| 2003/0208100 A1 | 11/2003 | Levy |
| 2003/0212391 A1 | 11/2003 | Fenton et al. |
| 2003/0233104 A1 | 12/2003 | Gellman et al. |
| 2003/0233108 A1 | 12/2003 | Gellman et al. |
| 2004/0034369 A1 | 2/2004 | Sauer et al. |
| 2004/0034372 A1 | 2/2004 | Chu |
| 2004/0044354 A1 | 3/2004 | Gannoe et al. |
| 2004/0059350 A1 | 3/2004 | Gordon et al. |
| 2004/0082963 A1 | 4/2004 | Gannoe et al. |
| 2004/0087979 A1 | 5/2004 | Field et al. |
| 2004/0088008 A1 | 5/2004 | Gannoe et al. |
| 2004/0092969 A1 | 5/2004 | Kumar |
| 2004/0122473 A1 | 6/2004 | Ewers et al. |
| 2004/0138682 A1 | 7/2004 | Onuki et al. |
| 2004/0147941 A1 | 7/2004 | Takemoto et al. |
| 2004/0147958 A1 | 7/2004 | Lam et al. |
| 2004/0162568 A1 | 8/2004 | Saadat et al. |
| 2004/0181243 A1 | 9/2004 | Chu et al. |
| 2004/0194790 A1 | 10/2004 | Laufer et al. |
| 2004/0210243 A1 | 10/2004 | Gannoe et al. |
| 2004/0260344 A1 | 12/2004 | Lyons et al. |
| 2005/0015101 A1 | 1/2005 | Gibbens, III et al. |
| 2005/0035007 A1 | 2/2005 | Kennedy et al. |
| 2005/0049638 A1 | 3/2005 | Mandelbaum |
| 2005/0055038 A1 | 3/2005 | Kelleher et al. |
| 2005/0070931 A1 | 3/2005 | Li et al. |
| 2005/0075653 A1 | 4/2005 | Saadat et al. |
| 2005/0209612 A1 | 9/2005 | Nakao |
| 2005/0216058 A1 | 9/2005 | Egan et al. |
| 2005/0262984 A1 | 12/2005 | Hetcher et al. |
| 2005/0267479 A1 | 12/2005 | Morgan et al. |
| 2006/0020274 A1 | 1/2006 | Ewers et al. |
| 2006/0069396 A1 | 3/2006 | Meade et al. |
| 2006/0111732 A1 | 5/2006 | Gibbens et al. |
| 2006/0224184 A1 | 10/2006 | Stefanchik et al. |
| 2006/0282089 A1 | 12/2006 | Stokes et al. |
| 2006/0282090 A1 | 12/2006 | Stokes et al. |
| 2006/0282091 A1 | 12/2006 | Shelton et al. |
| 2006/0282092 A1 | 12/2006 | Stokes et al. |
| 2006/0282093 A1 | 12/2006 | Shelton et al. |
| 2006/0282094 A1 | 12/2006 | Stokes et al. |
| 2006/0282095 A1 | 12/2006 | Stokes et al. |
| 2006/0282096 A1 | 12/2006 | Papa et al. |
| 2006/0282097 A1 | 12/2006 | Ortiz et al. |
| 2006/0282098 A1 | 12/2006 | Shelton et al. |
| 2006/0282099 A1 | 12/2006 | Stokes et al. |
| 2007/0135838 A1 | 6/2007 | Meyer |
| 2007/0239206 A1 | 10/2007 | Shelton et al. |
| 2008/0027468 A1 | 1/2008 | Fenton et al. |
| 2008/0086152 A1 | 4/2008 | McKay et al. |
| 2008/0132919 A1 | 6/2008 | Chui et al. |
| 2008/0140091 A1 | 6/2008 | DeDeyne et al. |
| 2008/0172071 A1 | 7/2008 | Barker |
| 2008/0210683 A1 | 9/2008 | Snell et al. |
| 2009/0018581 A1 | 1/2009 | Anderson et al. |
| 2009/0024145 A1 | 1/2009 | Meade et al. |
| 2009/0138002 A1 | 5/2009 | Fenton |
| 2009/0182353 A1 | 7/2009 | Snell et al. |
| 2009/0216269 A1 | 8/2009 | Harrington et al. |
| 2009/0223426 A1 | 9/2009 | Shonteff et al. |
| 2010/0036415 A1 | 2/2010 | Cabezas |
| 2010/0049219 A1 | 2/2010 | Cronin et al. |
| 2010/0130990 A1 | 5/2010 | Saliman |
| 2010/0152751 A1 | 6/2010 | Meade et al. |
| 2010/0191260 A1 | 7/2010 | Mohajer |
| 2011/0015760 A1 | 1/2011 | Kullas |
| 2011/0163634 A1 | 7/2011 | Kim et al. |
| 2011/0208320 A1 | 8/2011 | Stevenson et al. |

(56) References Cited

U.S. PATENT DOCUMENTS

| | | |
|---|---|---|
| 2011/0270279 A1 | 11/2011 | Badhwar |
| 2013/0046319 A1 | 2/2013 | Arnett et al. |
| 2013/0158568 A1* | 6/2013 | Kia .................... A61B 17/0469 606/144 |
| 2013/0178877 A1 | 6/2013 | Bender et al. |
| 2014/0163584 A1 | 6/2014 | Rohl et al. |
| 2014/0171977 A1 | 6/2014 | Martin et al. |
| 2014/0171979 A1 | 6/2014 | Martin et al. |
| 2014/0172015 A1 | 6/2014 | Martin et al. |
| 2015/0133967 A1 | 5/2015 | Martin |
| 2015/0351745 A1 | 12/2015 | Mumaw et al. |
| 2015/0351746 A1 | 12/2015 | Martin et al. |
| 2015/0351749 A1 | 12/2015 | Martin et al. |
| 2015/0351756 A1 | 12/2015 | Martin et al. |
| 2016/0242763 A1 | 8/2016 | Kia et al. |
| 2016/0317148 A1 | 11/2016 | Martinez |
| 2016/0331374 A1 | 11/2016 | Martin et al. |
| 2016/0345958 A1 | 12/2016 | Martin et al. |
| 2016/0346827 A1 | 12/2016 | Martin et al. |
| 2016/0361055 A1 | 12/2016 | Martin et al. |
| 2016/0367238 A1 | 12/2016 | Deck et al. |
| 2016/0367239 A1 | 12/2016 | Mumaw et al. |
| 2016/0367240 A1 | 12/2016 | Shelton, IV et al. |
| 2016/0367243 A1 | 12/2016 | Martin et al. |

FOREIGN PATENT DOCUMENTS

| | | |
|---|---|---|
| WO | 2010/138580 A2 | 12/2010 |
| WO | 2010138580 A3 | 12/2010 |

OTHER PUBLICATIONS

Rospatent. International Search Report and Written Opinion for International Application No. PCT/US2013/038746 (Brigham and Women's Hospital, Inc. et al.) dated Sep. 12, 2013, 7 pages.

EPO. Supplementary European Search Report for European Patent Application No. EP14850216.4 (Kia, Michael A. et al.) dated May 5, 2017, 4 pages.

EPO. Supplementary Partial European Search Report for European Patent Application No. EP14850216 4 (Kia, Michael A. et al.) dated May 15, 2017, 4 pages.

EPO. Provisional Opinion Accompanying the Partial European Search Result for European Patent Application No. EP14850216.4 (Kia, Michael A. et al.) dated May 15, 2017, 4 pages.

EPO. European Search Opinion for European Patent Application No. EP14850216.4 (Kia, Michael A. et al.) dated Aug. 18, 2017, 4 pages.

\* cited by examiner

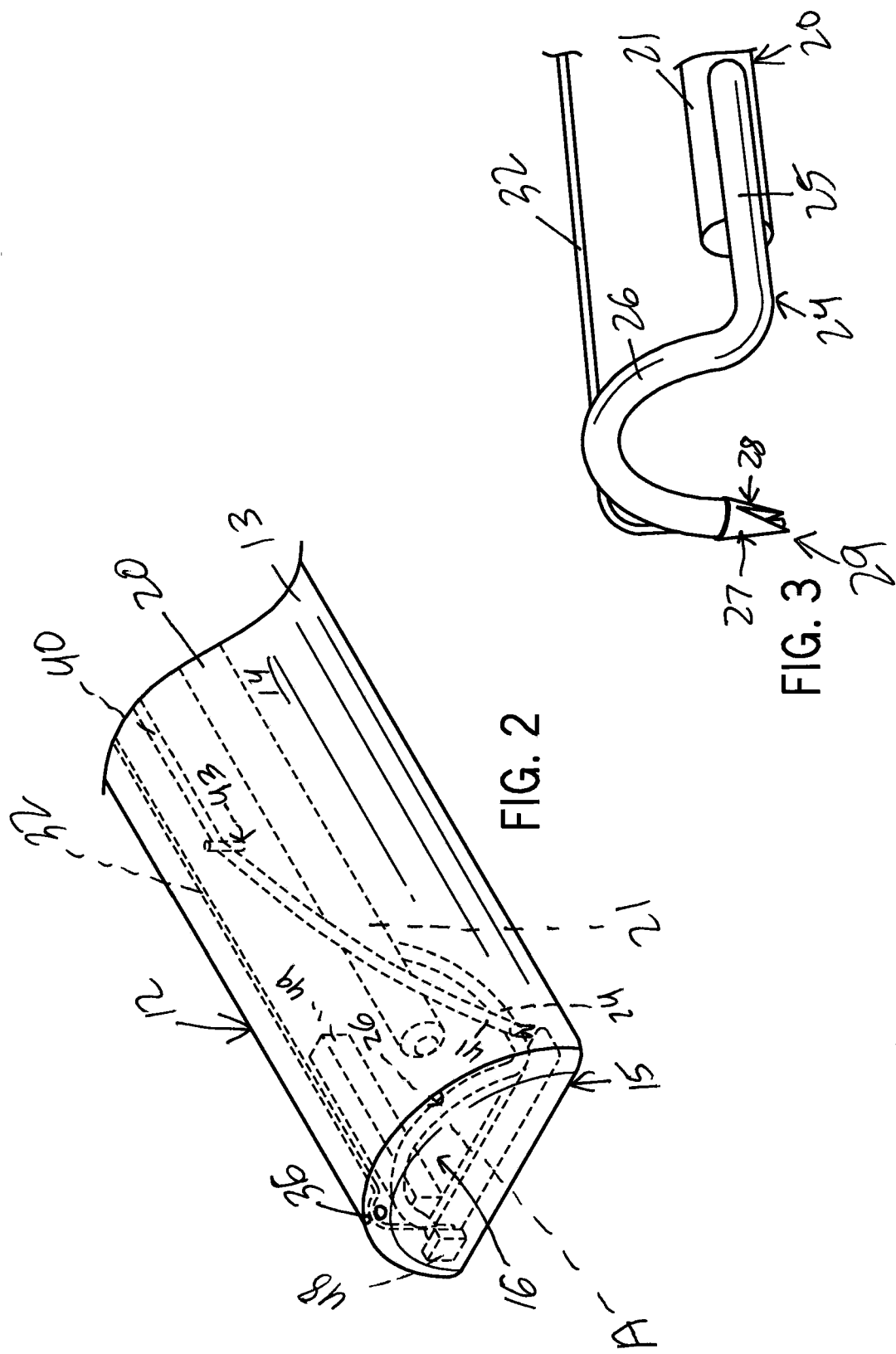

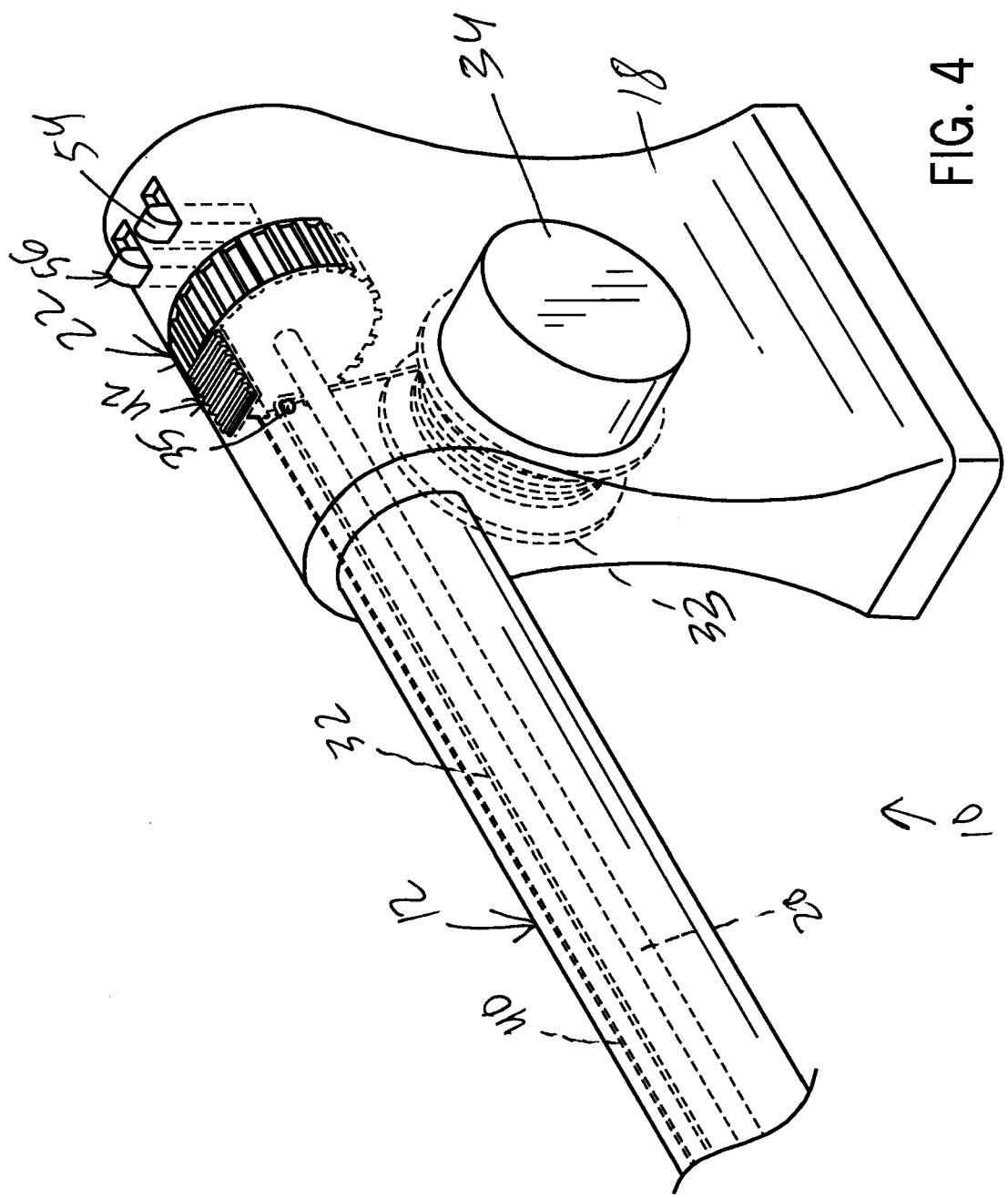

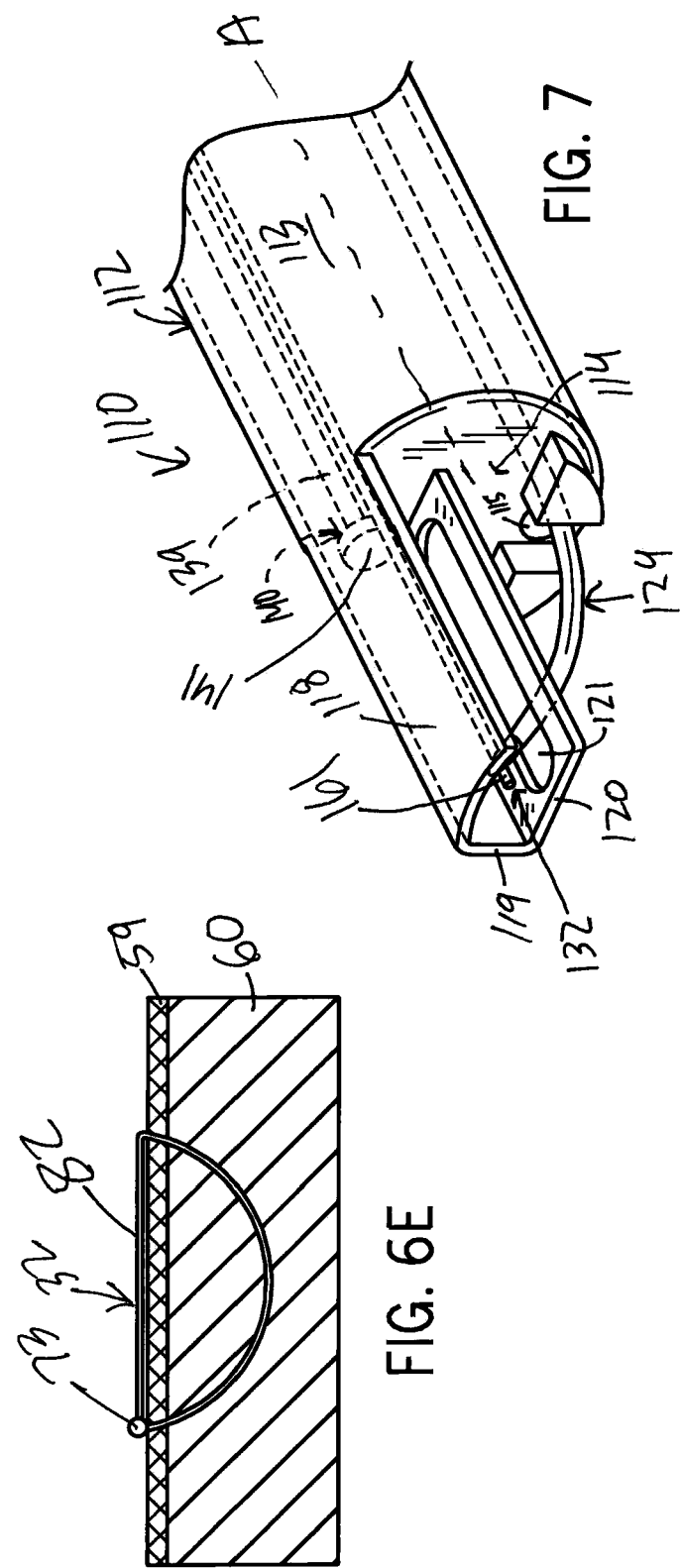
FIG. 7
FIG. 6E
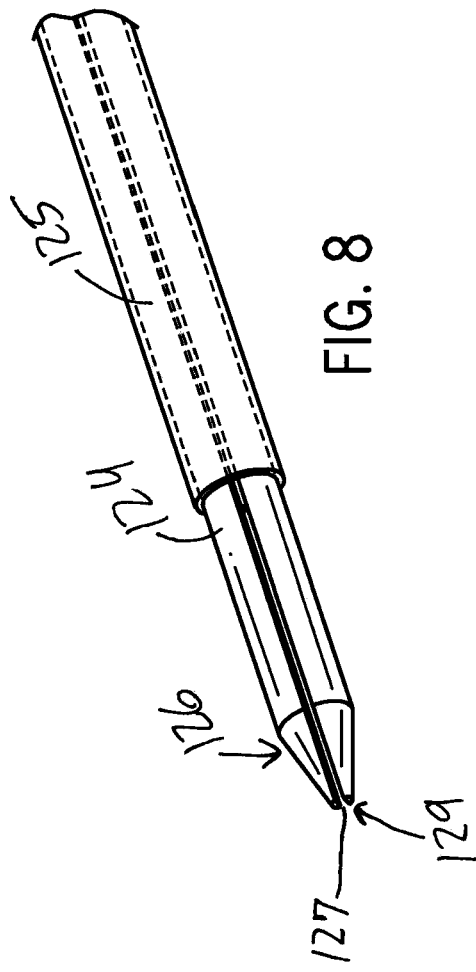
FIG. 8

SUTURING DEVICE FOR LAPAROSCOPIC PROCEDURES

CROSS-REFERENCE TO RELATED APPLICATIONS

This application is continuation of and claims the benefit of priority to U.S. patent application Ser. No. 15/987,733, filed May 23, 2018, which in turn is a continuation of U.S. patent application Ser. No. 14/397,682 filed Oct. 29, 2014, which in turn is a 371 application of PCT Application No. PCT/US2013/038746 filed Apr. 30, 2013, which claims the benefit of priority to U.S. Provisional Application Ser. No. 61/641,069 filed May 1, 2012. Each of the foregoing patent applications is incorporated herein by reference for all purposes.

STATEMENT REGARDING FEDERALLY SPONSORED RESEARCH

Not applicable.

FIELD

The disclosure relates to a suturing device suitable for laparoscopic procedures. In one non-limiting example surgical use, the suturing device is used in performing laparoscopic sacrocolpopexy or sacrocervicopexy.

BACKGROUND

Pelvic organ prolapse is a common medical condition, affecting almost half of women over the age of 50. (See, Subak et al., "Cost Of Pelvic Organ Prolapse Surgery In The United States", *Obstet Gynecol.* 2001; 98(4):646-651.) As the population in the United States ages, there will be an increasing number of women who require treatment for this condition. This medical condition results in lifestyle restriction, social limitations, sexual dysfunction, and pain, but can also lead to more critical conditions such as urinary retention, urinary tract infection, and sepsis.

Laparoscopic sacrocolpopexy is the current gold standard for the surgical treatment of apical pelvic organ prolapse. (See, Ganatra et al., "The Current Status Of Laparoscopic Sacrocolpopexy: A Review", *Eur Urol.* 2009. See, also, U.S. Pat. No. 6,592,515 and PCT International Publication No. WO 2011/037837.) Interest in laparoscopic mesh placement has increased considerably in the current environment of mesh erosion that is associated with transvaginal placement of mesh. Sacrocolpopexy suspends the apex of the vagina by affixing a Y-shaped piece of synthetic mesh to the anterior and posterior vaginal walls and suspending this from a strong ligament on the anterior part of the sacrum. This procedure is typically performed via a laparoscopic approach, entering the abdominal cavity to access the sacrum and vaginal tissues, both of which are retroperitoneal (behind the lining of the abdominal cavity). Tackers are not acceptable for use on the vagina, and laparoscopic mesh placement is quite challenging and requires advanced laparoscopic suturing skills in order to fasten the mesh.

Therefore, there is a need for a suturing device and associated method that can automate the process of fastening tissue and mesh laparoscopically and that enable a very rapid and secure fixation of mesh using a suturing material.

SUMMARY OF THE DISCLOSURE

The present disclosure provides implementations that satisfy the foregoing needs by providing a suturing device for laparoscopic procedures. In one form, the device is comprised of a handle and a five millimeter shaft. At the end of the shaft, there is a needle that drives a fusible suture through the tissue and a loop is formed. A fusion device is then fired on the two ends of the suture loop which fastens the sutures together to form a knot. The suture is also cut. The suture driving, knot forming and cutting are all done by manipulating features on the handle.

In one aspect of the disclosure, there is provided a device for suturing tissue in a patient. The suturing device includes an elongated body having an outer wall defining an interior space of the body, a rotatable shaft located in the interior space of the body, and a needle mounted on a distal end of the shaft. The needle has a distal section transverse to a longitudinal axis of the shaft. The distal section of the needle terminates in a first jaw and a second opposed jaw forming a forceps. At least one of the first jaw and the second jaw is movable relative to the other of the first jaw and the second jaw such that the first jaw and the second jaw have a grasping position in which the first jaw and the second jaw can grasp a suturing material and such that the first jaw and the second jaw have a release position in which the first jaw and the second jaw release the suturing material. The first jaw and the second jaw define a piercing tip of the needle when the first jaw and the second jaw are in the grasping position. In one form, the distal section of the needle is arcuate thereby forming a rotary needle. The suturing device can include a handle mounted to the elongated body, and the shaft can be fixed to a transverse disc shaped projection located on the handle for rotating the shaft.

The needle has a first position in which the piercing tip faces away from the interior space of the body, and the needle has a second position in which the piercing tip faces toward the interior space of the body. The rotary needle follows a curved path through tissue from the first position to the second position when the shaft is rotated about its longitudinal axis. The first jaw and the second jaw are in the grasping position thereby grasping the suturing material when the needle moves through tissue from the first position to the second position when the shaft is rotated about its longitudinal axis. The suturing material can be provided from a supply reel of suturing material, and a distal segment of suturing material is arranged in the interior space of the body such that the first jaw and the second jaw can grasp the suturing material when the needle is in the first position. The outer wall of the body can include a slot, and the needle passes through the slot when the needle moves from the first position to the second position when the shaft is rotated about its longitudinal axis.

The suturing device can further include a transfer arm located in the interior space of the body. The transfer arm terminates in a first holding member and a second opposed holding member. At least one of the first holding member and the second holding member is movable relative to the other of the first holding member and the second holding member such that the first holding member and the second holding member have a holding position in which the first holding member and the second holding member hold the suturing material and the first holding member and the second holding member have a disengaged position in which the first jaw and the second jaw disengage the suturing material.

The suturing device can further include an attachment device for securing together spaced apart portions of the suturing material thereby forming a closed length of the suturing material. In one form, the attachment device comprises a pair of heating elements movable between an open position in which the heating elements are spaced apart and a heat sealing position for contacting the spaced apart portions of the suturing material and heat sealing the spaced apart portions of the suturing material together.

The suturing material can be transferred from the first jaw and the second jaw of the needle to the first holding member and the second holding member of the transfer arm when the needle is in the second position, and the transfer arm can orient the spaced apart portions of the suturing material between the heating elements when the heating elements are in the open position. The heating elements are moved into the heat sealing position for contacting the spaced apart portions of the suturing material and heat sealing the spaced apart portions of the suturing material together.

In one form of the suturing device, a button is located on the handle of the suturing device, and a proximal end of the transfer arm is fixed to the button for moving the transfer arm. In another form of the suturing device, a first lever is located on the handle, and the first jaw and the second jaw are operatively coupled to the first lever such that movement of the first lever moves the first jaw and the second jaw between the grasping position and the release position. In yet another form of the suturing device, a second lever is located on the handle, and the first holding member and the second holding member are operatively coupled to the second lever such that movement of the second lever moves the first holding member and the second holding member between the holding position and the disengaged position.

In another aspect of the disclosure, there is provided method for suturing tissue in a patient. The method for suturing tissue uses a suturing device including an elongated body having an outer wall defining an interior space of the body, a rotatable shaft located in the interior space of the body, and a needle mounted on a distal end of the shaft. The needle has a distal section transverse to a longitudinal axis of the shaft, and the distal section of the needle terminates in a first jaw and a second opposed jaw. At least one of the first jaw and the second jaw is movable relative to the other of the first jaw and the second jaw. A leading portion of a length of suturing material is grasped within the interior space of the body with the first jaw and the second jaw of the needle such that the first jaw and the second jaw define a piercing tip, and the piercing tip is located near the tissue.

The shaft is rotated about its longitudinal axis thereby penetrating the tissue at an entry point of the tissue. The rotation of the shaft is continued until the leading portion of the length of suturing material has passed through the tissue and out of an exit point of the tissue. The leading portion of the length of suturing material is moved to a location near the entry point such that the leading portion of the length of suturing material is near or contacts a trailing portion of the length of suturing material. The leading portion of the length of suturing material and the trailing portion of the length of suturing material are attached together thereby forming a closed length of the suturing material.

In one version of the method, the leading portion of the length of suturing material is moved to the location near the entry point using a transfer arm located in the interior space of the body. In one version of the method, the leading portion of the length of suturing material and the trailing portion of the length of suturing material are fused together using a pair of heating elements that are moved into contact with the leading portion and the trailing portion of the length of suturing material. The length of suturing material can be provided from a supply of suturing material located in the device.

In one version of the method, a mesh is placed over the tissue and thereafter the shaft is rotated about its longitudinal axis thereby penetrating the mesh and the tissue at the entry point. The method can fasten the mesh and the tissue laparoscopically. In one non-limiting example, the method is used in performing laparoscopic sacrocolpopexy or sacrocervicopexy.

In yet another aspect of the disclosure, there is provided a device for suturing tissue in a patient. The suturing device includes an elongated body having an outer wall defining an interior space of the body, and a needle positioned inside the body for translating in the body. A distal end of the needle terminates in a piercing tip suitable for grasping a suturing material. The piercing tip is movable between a first position in which the piercing tip is positioned in a first section of the interior space of the body and a second position in which the piercing tip is positioned in a second section of the interior space of the body. A length of suturing material is arranged in the second section of the interior space of the body. The piercing tip of the needle follows a first path when moving from the first position to the second position in which the piercing tip exits the first section of the interior space of the body, enters and exits an external space located outside of the body, and enters the second section of the interior space of the body where the piercing tip of the needle grasps a leading portion of the length of suturing material. The piercing tip of the needle follows a second path when moving from the second position to the first position in which the piercing tip exits the second section of the interior space of the body, enters and exits the external space, and is positioned near or in the first section of the interior space of the body. Preferably, the first path and the second path are substantially the same. The first path and/or the second path may be curved. The suturing material can be provided from a supply of suturing material, and a distal segment of suturing material is arranged in the second section of the interior space of the body such that the piercing tip can grasp the suturing material when the needle is in the second position.

The suturing device further includes an attachment device for securing together a leading portion of the length of suturing material and a trailing portion of the length of suturing material thereby forming a closed length of the suturing material. The leading portion of the length of suturing material and the trailing portion of the length of suturing material are positioned near each other when the piercing tip of the needle is at an end of the second path. The attachment device can be include a heating element movable between an initial position and a heat sealing position for placing the leading portion of the length of suturing material and the trailing portion of the length of suturing material in contact and heat sealing the leading portion of the length of suturing material and the trailing portion of the length of suturing material together. The attachment device can be a plunger that terminates in the heating element. The plunger can move transversely with respect to a longitudinal axis of the body when the plunger moves between the initial position and the heat sealing position.

In one form, the piercing tip of the needle has a slit for receiving the leading portion of the length of suturing material thereby grasping the leading portion of the length of suturing material in the piercing tip of the needle. In one form, the second section of the interior space of the body comprises a hollow extension that extends longitudinally outward beyond the first section of the interior space of the body.

In still another aspect of the disclosure, there is provided method for suturing tissue in a patient. The method uses a suturing device including an elongated body having an outer wall defining an interior space of the body, and a needle positioned inside the body for translating in the body. A distal end of the needle terminates in a piercing tip suitable for grasping a suturing material. The piercing tip is movable between a first position in which the piercing tip is positioned in a first section of the interior space of the body and a second position in which the piercing tip is positioned in a second section of the interior space of the body. The piercing tip is located near the tissue with the piercing tip in the first position. The piercing tip is moved from the first position to the second position such that the piercing tip exits the first section of the interior space of the body, enters and exits tissue positioned in an external space located outside of the body of the device, and enters the second section of the interior space of the body where the piercing tip of the needle grasps a leading portion of the length of suturing material. The length of suturing material can be provided from a supply of suturing material located in the device.

The piercing tip and the leading portion of the length of suturing material are moved from the second position to the first position in which the piercing tip and the leading portion of the length of suturing material exit the second section of the interior space of the body, enter and exit the tissue positioned in the external space, and are positioned near or in the first section of the interior space of the body. A trailing portion of the length of suturing material is then moved to a location near the leading portion of the length of suturing material. The leading portion of the length of suturing material and the trailing portion of the length of suturing material are then attached thereby forming a closed length of the suturing material.

The trailing portion of the length of suturing material can be moved to the location near the leading portion of the length of suturing material using a plunger located in the body. The leading portion of the length of suturing material and the trailing portion of the length of suturing material can be fused together using a heating element on the plunger wherein the heating element is moved into contact with at least one of the leading portion and the trailing portion of the length of suturing material. The plunger can move the trailing portion of the length of suturing material laterally with respect to a longitudinal axis of the body.

A mesh can be placed over the tissue before locating the piercing tip near the tissue. The piercing tip and the leading portion of the length of suturing material can be moved through the mesh. In one version of the method, the mesh and the tissue are fastened laparoscopically. In one non-limiting example, the method is used in performing laparoscopic sacrocolpopexy or sacrocervicopexy.

These and other features, aspects, and advantages of the present disclosure will become better understood upon consideration of the following detailed description, drawings, and appended claims.

BRIEF DESCRIPTION OF THE DRAWINGS

FIG. 2 is a top, right detailed perspective view of the distal end of the suturing device of FIG. 1.

FIG. 3 is a side view of the needle of the suturing device of FIG. 1.

FIG. 4 is a top, right detailed perspective view of the proximal end of the suturing device of FIG. 1.

FIG. 6E is a cross-sectional view of a suture with a fused length of the suturing material prepared using the suturing device of FIG. 1.

FIG. 7 is a top, right detailed perspective view of a second embodiment of a suturing device in accordance with the disclosure.

FIG. 8 is a top, right detailed perspective view of the needle of the suturing device of FIG. 7.

Like reference numerals will be used to refer to like parts from Figure to Figure in the following description of the drawings.

DETAILED DESCRIPTION

Figure 1:
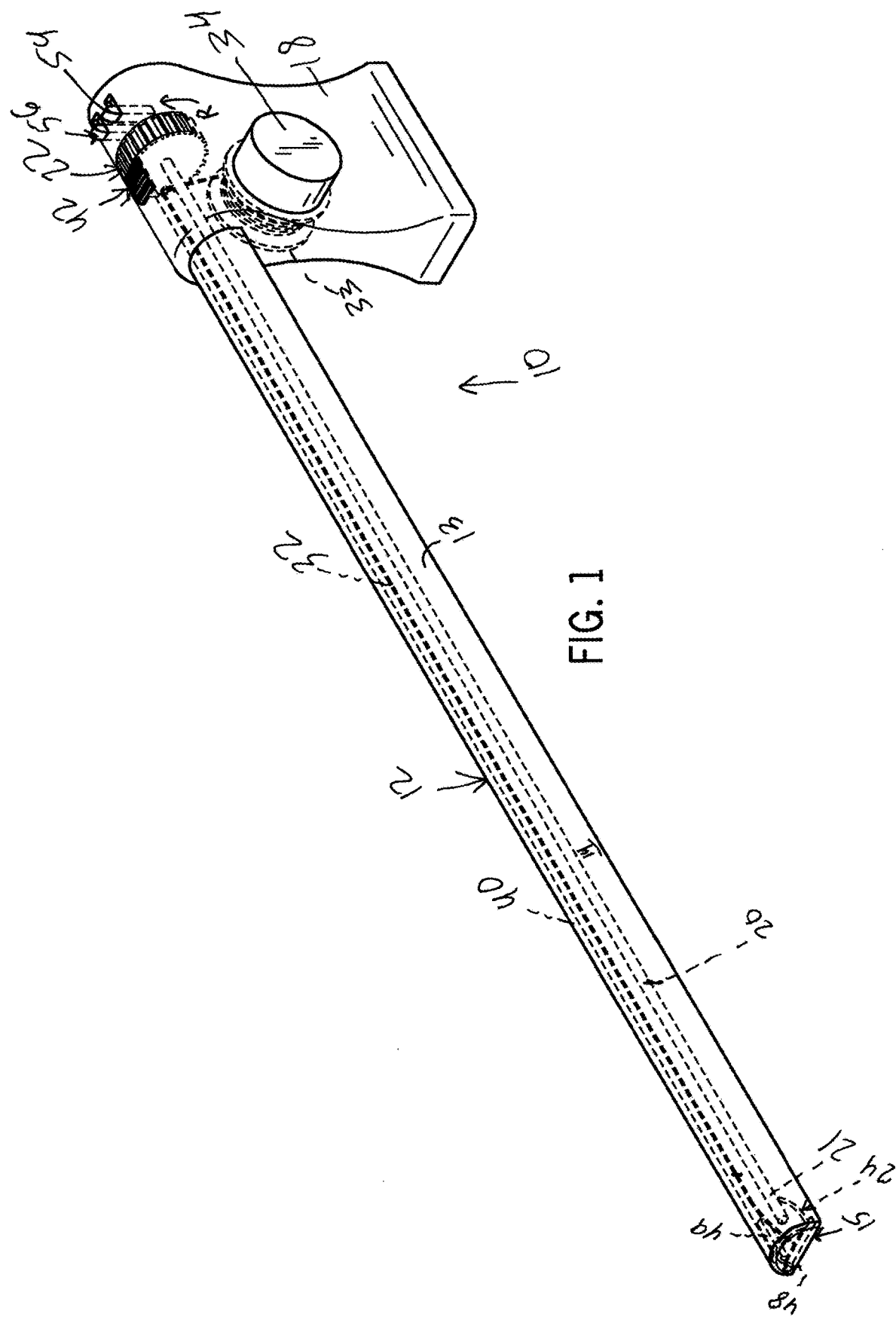
FIG. 1 is a top, right perspective view of a first embodiment of a suturing device according to the disclosure.

Referring to FIGS. 1 to 6E, there is shown a first embodiment of a suturing device 10 having an elongated body 12 with an outer wall 13 including first wall section 14 having a generally semi-circular shape in a cross-section transverse to a longitudinal axis A of the body 12, and a second flat wall section 15. The outer wall 13 defines an interior space 16 of the body 12. The interior space 16 generally has a semi cylindrical shape. The body 12 may comprise a polymeric material such as polyethylene or polypropylene. The suturing device 10 includes a handle 18 attached to the body 12. The surgeon can hold on to the suturing device 10 by the handle 18 which may also comprise a polymeric material such as polyethylene or polypropylene. The body 12 of the suturing device 10 can be introduced through an anatomical cavity wall using known laparoscopic surgical techniques. Suitable illumination devices (e.g. optical fibers) can be provided in one or more lumens of the body 12, or can be provided in a separate device that is introduced through the anatomical cavity wall using known laparoscopic surgical techniques. The suturing device 10 includes a rotatable hollow shaft 20 located centrally in the interior space 16 of the body 12. The shaft 20 has a distal end 21 and a transverse projection 22 fixed to the proximal end of the shaft 20 for rotating the shaft. In the embodiment of the suturing device 10 shown, the projection 22 is disc shaped and includes surface notches for a good grip.

The suturing device 10 includes a hollow needle 24 having a shank 25 and a distal section 26. The distal section 26 is transverse to the longitudinal axis A of the shaft 20. A first jaw 27 and a second opposed jaw 28 are located at the end of the distal section 26 of the needle 24. The first jaw 27 and the second jaw 28 are movable relative to each other. This can be accomplished by one of the first jaw 27 and the second jaw 28 being movable, or both of the first jaw 27 and the second jaw 28 being movable. Operation of the first jaw 27 and the second jaw 28 will be further described below. The first jaw 27 and the second jaw 28 define a piercing tip 29 of the needle 24.

The suturing device 10 includes a continuous length of a suturing material 32. The suturing material 32 is provided on a supply reel 33 with an attached feed knob 34 that can be rotated to feed the suturing material 32 from the reel 33. A first feed guide 35 and a second feed guide 36 keep the suturing material 32 suitably tensioned in the interior space 16 of the body 12 when feeding the suturing material 32. The suturing material 32 is preferably thermoplastic to allow for heat sealing of sections of the suturing material 32 together. The suturing material 32 can be, for example, an absorbable material, such as polyglycolic acid, polylactic acid, and polydioxanone, or a non-absorbable material such as nylon and polypropylene (e.g. Prolene®).

The suturing device 10 includes a hollow transfer arm 40 having a distal end 41 and a push button 42 at its proximal end. A positioner 43 is located near the distal end 41 of the transfer arm 40. A first holding member 44 (see FIG. 6A) and a second holding member 45 (see FIG. 6A) are located at the distal end 41 of the transfer arm 40. The first holding member 44 and the second holding member 45 are movable relative to each other. This can be accomplished by one of the first holding member 44 and the second holding member 45 being movable, or both of the first holding member 44 and the second holding member 45 being movable. Operation of the first holding member 44 and the second holding member 45 will be further described below.

The suturing device 10 includes a first fusion block 48 and a second fusion block 49. The first fusion block 48 and the second fusion block 49 fuse spaced apart portions of the length of suturing material 32 together as described below. The first fusion block 48 and the second fusion block 49 each include heating element sections that are resistance heated by a suitable source of electricity such as a battery or external AC power supply. Alternatively, just one of the first fusion block 48 and the second fusion block 49 includes a heating element section. The first fusion block 48 and the second fusion block 49 are movable relative to each other. This can be accomplished by one of the first fusion block 48 and the second fusion block 49 being movable, or both of the first fusion block 48 and the second fusion block 49 being movable. In one form, the second fusion block 49 is attached to a guide wire that has a proximal lever on the handle 18. The proximal lever can move the second fusion block 49, which is arranged in a suitable guide support, toward and away from the first fusion block 48.

Figure 5:
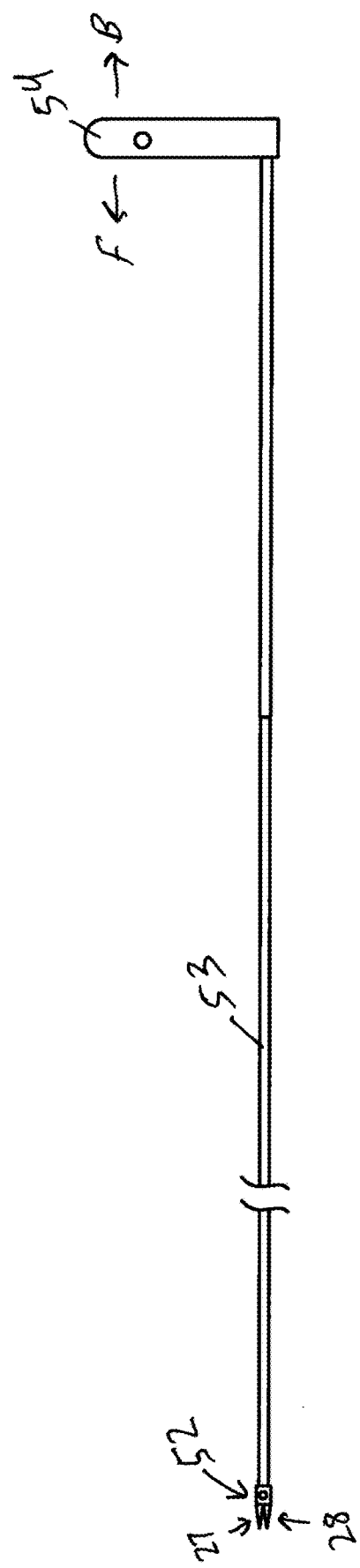
FIG. 5 is a side view of needle jaws with a guide wire and associated lever of the suturing device of FIG. 1.

Looking now at FIG. 5, operation of the first jaw 27 and the second jaw 28 of the needle 24 can be further described. The first jaw 27 and the second jaw 28 are connected to a first linkage 52 that is attached to a first guide wire 53 having a first lever 54 at its proximal end. The first lever 54 protrudes through the top of the handle 18 (see FIGS. 1 and 4). The first guide wire 53 is contained in the hollow shaft 20 and the hollow needle 24. The first linkage 52 mounts the first jaw 27 and the second jaw 28 at the end of the distal section 26 of the needle 24. Moving the first lever 54 in direction F in FIG. 5 causes the first jaw 27 and the second jaw 28 of the needle 24 to come together, and moving the first lever 54 in direction B in FIG. 5 causes the first jaw 27 and the second jaw 28 of the needle 24 to move apart. Movement of one or both of the first jaw 27 and the second jaw 28 can accomplish this, and the first linkage 52 can be suitably designed to move either one or both of the first jaw 27 and the second jaw 28 when the first lever 54 is moved.

Likewise, the first holding member 44 and the second holding member 45 are connected to a second linkage that is attached to a second guide wire having a second lever 56 at its proximal end. The second lever 56 protrudes through the top of the handle 18 (see FIGS. 1 and 4). The second guide wire is contained in the hollow transfer arm 40. The second linkage mounts the first holding member 44 and the second holding member 45 at the distal end of the hollow transfer arm 40. Moving the second lever 56 in direction F in FIG. 5 causes the first holding member 44 and the second holding member 45 of the transfer arm 40 to come together, and moving the second lever 56 in direction B in FIG. 5 causes the first holding member 44 and the second holding member 45 of the transfer arm 40 to move apart. Movement of one or both of the first holding member 44 and the second holding member 45 can accomplish this, and the second linkage can be suitably designed to move either one or both of the first holding member 44 and the second holding member 45 when the second lever 56 is moved.

Figure 6A:
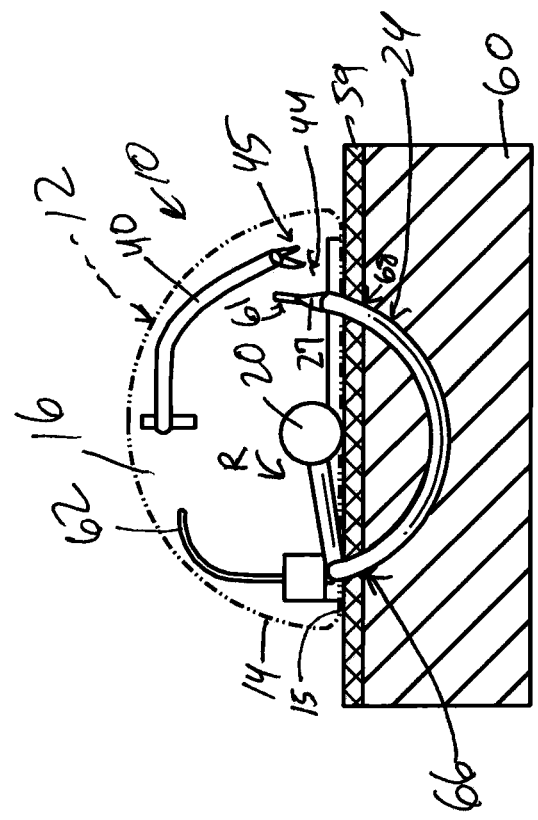
FIG. 6A is a cross-sectional view of the suturing device of FIG. 1 beginning a suturing method in accordance with the disclosure.

Looking now at FIGS. 6A to 6E, operation of the suturing device 10 in suturing tissue can be explained. In FIG. 6A, the suturing device 10 is in its initial position, and the second wall section 15 of the body 12 has been placed in contact with a mesh 59 placed on tissue 60. One non-limiting mesh is a polypropylene mesh. The first lever 54 is moved in direction F (as shown in FIG. 5) which causes the first jaw 27 and the second jaw 28 of the needle 24 to come together to grasp a leading portion 61 of the suturing material 32. A trailing portion 63 of the suturing material 32 is located in the body 12.

The shaft 20 is then rotated in direction R by moving projection 22 in direction R on the handle 18 (see FIG. 1). The piercing tip 29 of the needle 24 passes through a slot 71 (see FIG. 6D) in the second wall section 15 of the body 12 and then penetrates the mesh 59 and an entry point 66 of the tissue 60. By continuing to rotate the shaft 20 in direction R, the piercing tip 29 and the leading portion 61 of the length of suturing material 32 pass through the mesh 59 and the tissue 60 at an exit point 68. The needle 24 and the leading portion 61 of the length of suturing material 32 are then in the position shown in FIG. 6B. Thus, the needle 24 holds the suturing material 32 and pierces the mesh 59 and tissue layer 60 and moves in a rotary path with the suturing material 32 following the rotary path of the needle 24. In FIG. 6B, it can be seen that the transfer arm 40 has located the first holding member 44 and the second holding member 45 near the leading portion 61 of the length of suturing material 32.

Figure 6D:
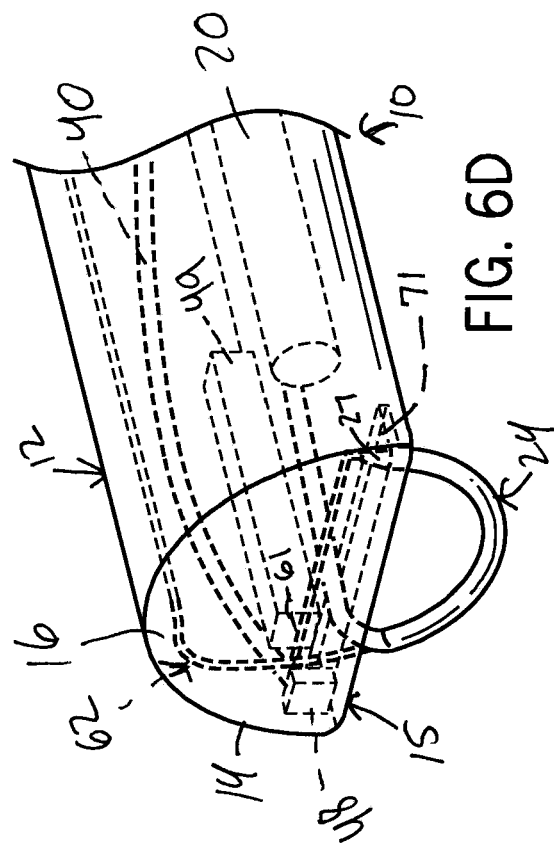
FIG. 6D is a top, right detailed perspective view of the suturing device of FIG. 1 after the transfer arm has moved a leading portion of a length of the suturing material next to a trailing portion of the length of suturing material before fusing the length of the suturing material.
Figure 6B:
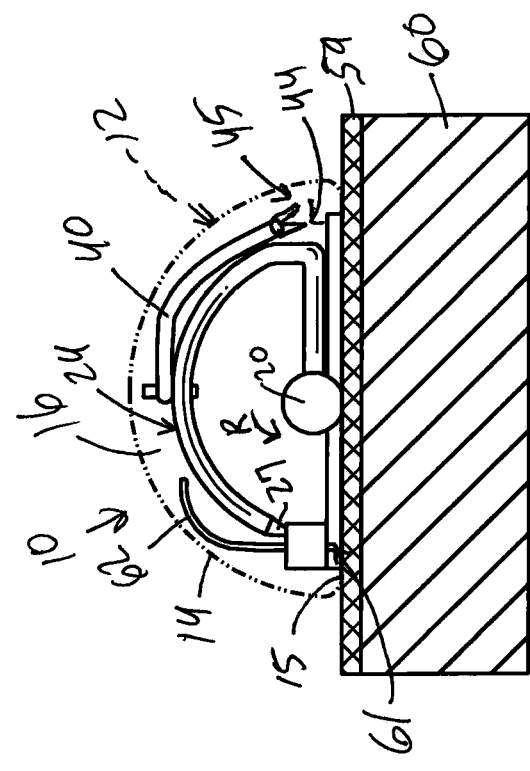
FIG. 6B is a cross-sectional view of the suturing device of FIG. 1 after the piercing tip of the needle and attached suturing material have entered and exited tissue of the patient.
Figure 6C:
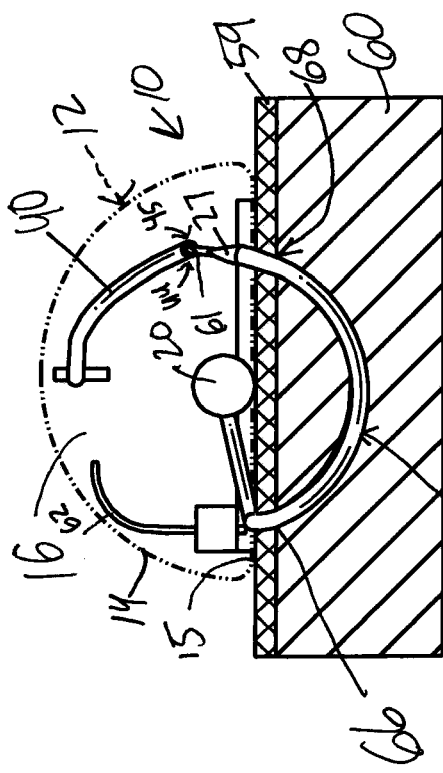
FIG. 6C is a cross-sectional view of the suturing device of FIG. 1 during transfer of the suturing material from the piercing tip of the needle to the transfer arm.

Referring now to FIG. 6C, the first holding member 44 and the second holding member 45 of the transfer arm 40 are moved next to the leading portion 61 of the length of suturing material 32 by way of button 42 on the handle 18 (see FIG. 1). Movement of the second lever 56 in direction F in FIG. 5 causes the first holding member 44 and the second holding member 45 of the transfer arm 40 to come together and grasp the leading portion 61 of the length of suturing material 32 as shown in FIG. 6C. The button 42 on the handle 18 can then be rotated transverse to the longitudinal axis A of the body 12. This moves the leading portion 61 of the length of suturing material 32 to a location near the entry point 66 of the tissue 60 such that the leading portion 61 of the length of suturing material 32 is near or contacts the trailing portion 62 of the length of suturing material 32. The leading portion 61 and the trailing portion 62 of the length of suturing material 32 intersect between the first fusion block 48 and the second fusion block 49. This is shown in FIG. 6D.

When the leading portion 61 and the trailing portion 62 of the length of suturing material 32 are in the position shown in FIG. 6D, the heating element sections of the first fusion block 48 and the second fusion block 49 are brought together on the leading portion 61 and the trailing portion 62 of the length of suturing material 32, and the heating elements are resistance heated. This heat seals together the leading portion 61 of the length of suturing material 32 and the trailing portion 62 of the length of suturing material 32 at a fusion point 73 as shown in FIG. 6E, thereby forming a closed length 82 of the suturing material 32. After fusion of suturing material 32, a cutter on the first fusion block 48 and/or the second fusion block 49 cuts the suturing material 32 near the fusion point 73. The needle 24 can then be rotated back to the initial position shown in FIG. 6A by moving projection 22 on the handle 18 in a direction opposite to direction R. The steps described above with reference to FIGS. 6A to 6E can then be repeated to create another closed length 82 of the suturing material 32 at a different location on the mesh 59 and the tissue 60.

Thus, operation of the suturing device 10 as shown in FIGS. 6A to 6E can be summarized as follows: (1) the suturing device 10 is provided with pre-loaded reel 33 of suturing material 32; (2) the leading portion 61 of the length of suturing material 32 is grasped by the jaws 27, 28 of the rotary needle 24 by moving the first lever 54; (3) the rotary needle 24 pierces the mesh 59 and the tissue 60; (4) the leading portion 61 of the length of suturing material 32 is picked up by the holding members 44, 45 of the transfer arm 40 by moving the second lever 56; (5) the leading portion 61 of the length of suturing material 32 is then taken back near the initial position of the piercing tip 29 of the needle 24; (6) the fusion blocks 48, 49 are then operated; (7) the rotary needle 24 is reverted back to the initial position; and (8) the procedure is repeated for the next suturing.

Although FIGS. 6A-6E describe attaching together the leading portion 61 and the trailing portion 62 of the length of suturing material 32 using fusion blocks 48, 49 to create a heat sealed fusion point 73, alternative methods such as knotting, metal strips, plastic strips, and glue can be used for attaching together the leading portion 61 and the trailing portion 62 of the length of suturing material 32 to form the closed length 82 of the suturing material 32.

Referring now to FIGS. 7 to 9D, there is shown a second embodiment of a suturing device 110 having an elongated body 112 including a main outer wall 113 and a transverse wall 114 with an opening 115. The body 112 defines an interior space 116 of the suturing device 110, and the body 112 has a longitudinal axis A. The body 112 can comprise a polymeric material such as polyethylene or polypropylene. The body 112 includes a top extension wall 118, a side extension wall 119, and a bottom extension wall 120 that extend longitudinally outward from the body 112. The bottom extension wall 120 includes an oblong slot 121.

The suturing device 110 includes a handle (similar to handle 18 in FIG. 1) attached to the body 112. The surgeon can hold on to the suturing device 110 by the handle, which may also comprise a polymeric material such as polyethylene or polypropylene. The body 112 of the suturing device 110 can be introduced through an anatomical cavity wall using known laparoscopic surgical techniques. Suitable illumination devices (e.g. optical fibers) can be provided in one or more lumens of the body 112, or can be provided in a separate device that is introduced through the anatomical cavity wall using known laparoscopic surgical techniques.

The suturing device 110 includes a needle 124 that slidingly translates in a sleeve 125 (see FIG. 8). The needle 124 has a distal section 126 having a longitudinal slit 127. The distal section 126 of the needle 124 defines a piercing tip 129 of the needle 124.

The suturing device 110 includes a continuous length of a suturing material 132. The suturing material 132 is provided on a supply reel with an attached feed knob that can be rotated to feed the suturing material 132 from the reel (similar to reel 33 and feed knob 34 in FIG. 1). Suitable feed guides keep the suturing material 132 suitably tensioned in the interior space 116 of the body 112 when feeding the suturing material 132. The suturing material 132 is preferably thermoplastic to allow for heat sealing of sections of the suturing material 132 together. The suturing material 132 can be, for example, an absorbable material, such as polyglycolic acid, polylactic acid, and polydioxanone, or a non-absorbable material such as nylon and polypropylene (e.g. Prolene®).

The suturing device 110 includes a suturing material attachment mechanism. A guide wire 139 includes a plunger 140 that terminates in a heating element 141. The heating element 141 is resistance heated by a suitable source of electricity such as a battery or external AC power supply. A plunger guide 143 transitions the plunger 140 from proximal to distal motion to motion transverse to the longitudinal axis A of the body 112.

Figure 9A:
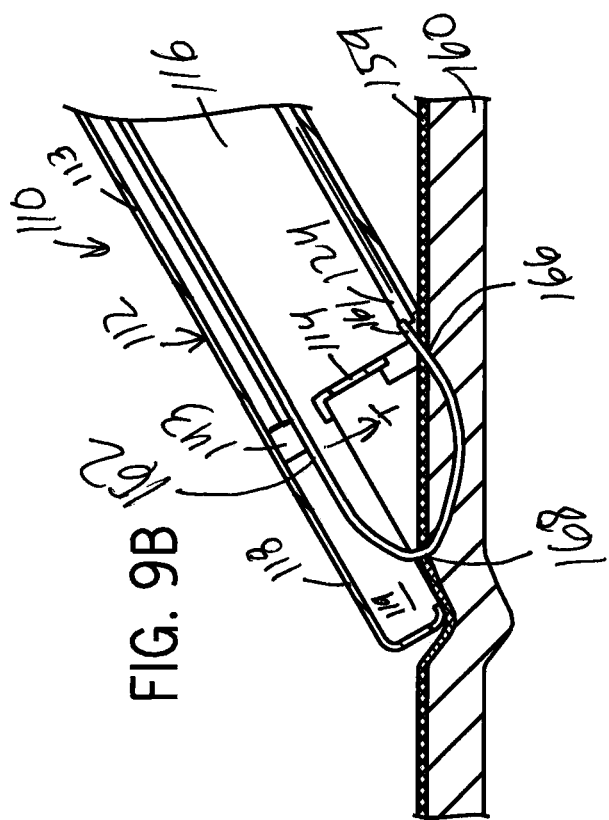
FIG. 9A is a cross-sectional view of the suturing device of FIG. 7 after the piercing tip of the needle has entered an entry point of the tissue and exited an exit point tissue of the patient.

Looking now at FIGS. 7 and 9A to 9D, operation of the suturing device 110 in suturing tissue can be explained. In FIG. 9A, a mesh 159 has been placed on tissue 160. One non-limiting example mesh is a polypropylene mesh. The needle 124 has been advanced in the sleeve 125 and the piercing tip 129 of the needle 124 has penetrated the mesh 159 and an entry point 166 of the tissue 160, and has passed through the tissue 160 at an exit point 168 and the mesh 159, and has passed through the slot 121 into a section of the interior space 116 defined by the top extension wall 118, the side extension wall 119, and the bottom extension wall 120 that extend longitudinally outward from the body 112. The slit 127 of the needle 124 has grasped a leading portion 161 of the length of suturing material 132. This position is shown in FIGS. 7 and 9A.

Figure 9D:
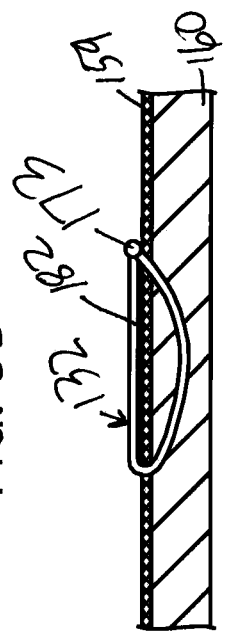
FIG. 9D is a cross-sectional view of a suture with a fused length of the suturing material prepared using the suturing device of FIG. 7.
Figure 9B:
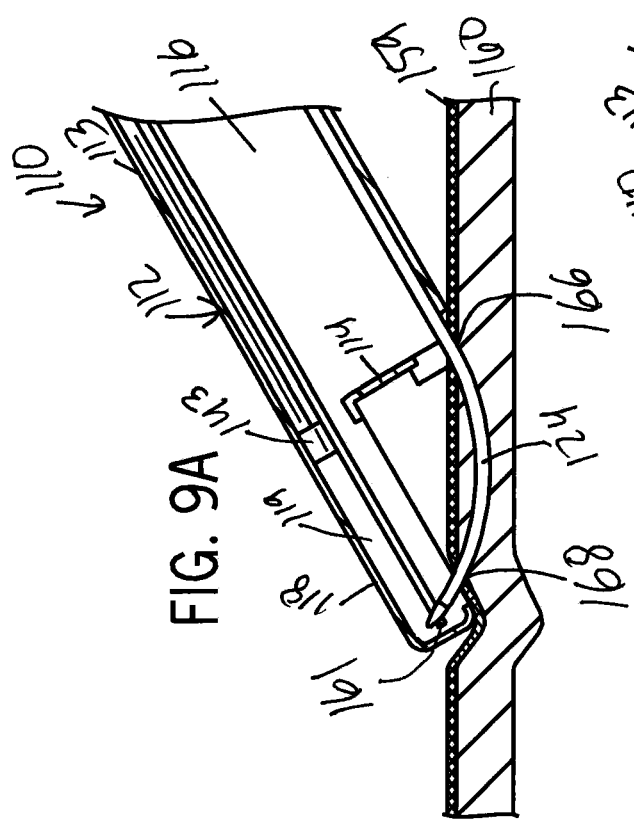
FIG. 9B is a cross-sectional view of the suturing device of FIG. 7 after the piercing tip of the needle has pulled attached suturing material back through the entry point of the tissue of the patient.

Referring now to FIG. 9B, the needle 124 has been retracted in the sleeve 125 and the piercing tip 129 and the leading portion 161 of the length of suturing material 132 have passed through the mesh 159 and the tissue 160 at the exit point 168, and have passed through the tissue 160, and have passed through the tissue 160 at the entry point 166 and the mesh 159. The needle 124 and the leading portion 161 of the length of suturing material 132 are then in the position shown in FIG. 9B in which the leading portion 161 of the length of suturing material 132 is positioned near or in a section of the interior space 116 of the body 112.

Figure 9C:
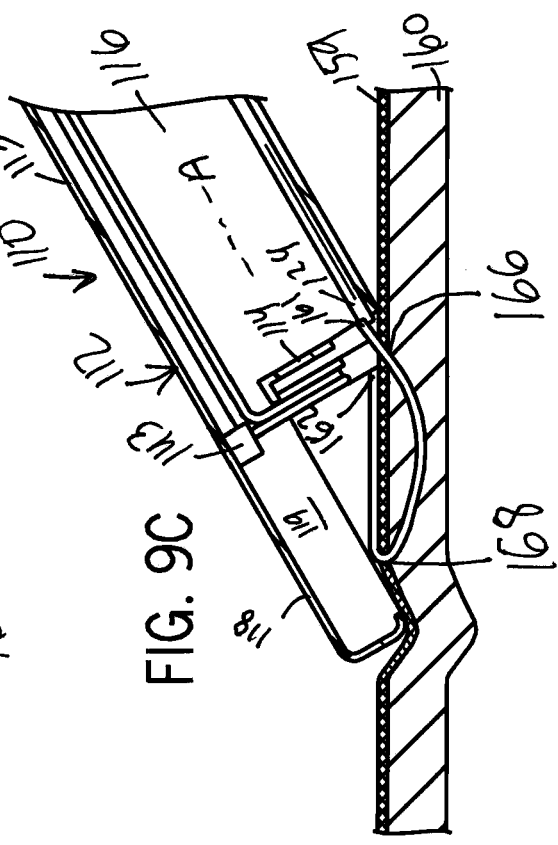
FIG. 9C is a cross-sectional view of the suturing device of FIG. 7 after the plunger head has moved a trailing portion of a length of the suturing material next to a leading portion of the length of suturing material.

When the leading portion 161 of the length of suturing material 132 is in the position in FIG. 6B, the plunger 140 with heating element 141 exits the plunger guide 143 and moves transverse to the longitudinal axis A of the body 112. See direction T in FIG. 9B. The end surface of the plunger 140 contacts a trailing portion 162 of the length of suturing material 132 and moves the trailing portion 162 of the length of suturing material 132 into contact with the leading portion 161 of the length of suturing material 132 as shown in FIG. 9C. The heating element 141 is resistance heated, and this fuses together the leading portion 161 of the length of suturing material 132 and the trailing portion 162 of the length of suturing material 132 at a fusion point 173 as shown in FIG. 9D, thereby forming a closed length 182 of the suturing material 132. After fusion of suturing material 132, a cutter on the plunger 140 cuts the suturing material 132 near the fusion point 173. The steps described above with reference to FIGS. 9A to 9D can then be repeated to create another closed length 182 of the suturing material 132 at a different location on the mesh 159 and the tissue 160.

Looking at FIGS. 9A and 9B, the needle 124 follows a generally curved path between the entry point 166 of the tissue 160 and the exit point 168 of the tissue 160. The distal section 126 of the needle 124 can be formed of a highly elastic material (e.g., a superelastic nickel-titanium alloy) to facilitate the curved path through the tissue 160. Specifically, the distal section 126 of the needle 124 can have a curved shape similar to the curved path desired through the tissue 160. When located in the sleeve 125, the curved shape of the distal section 126 of the needle 124 can assume the straight configuration of the inner space of the sleeve 125. When the distal section 126 of the needle 124 is moved out of the distal end of the sleeve 125 and through the opening 115 in the transverse wall 114 of the body 112, the distal section 126 of the needle 124 elastically returns to a curved shape similar to the curved path desired through the tissue 160. Preferably, the needle 124 follows substantially the same generally curved path when moving in either direction between the entry point 166 of the tissue 160 and the exit point 168 of the tissue 160. However, as long as the length of suturing material 132 is guided through the tissue 160, the path of the needle can vary when moving in opposite directions between the entry point 166 of the tissue 160 and the exit point 168 of the tissue 160.

Thus, the disclosure provides suturing devices and associated methods that can automate the process of fastening tissue and mesh laparoscopically. While the suturing devices are especially advantageous for performing laparoscopic sacrocolpopexy or sacrocervicopexy, the suturing devices can be used in any procedure where tissue is sutured.

Although the present invention has been described in detail with reference to certain embodiments, one skilled in the art will appreciate that the present invention can be practiced by other than the described embodiments, which have been presented for purposes of illustration and not of limitation. Therefore, the scope of the invention should not be limited to the description of the embodiments contained herein.

What is claimed is:

1. A suturing device having an articulable curved needle configured to facilitate advancement of a suture material through tissue, the suturing device defining a longitudinal axis along its length, the suturing device further including a first fusion element and a second fusion element, the first fusion element including a heating element that is displaceable along a direction parallel to the longitudinal axis within the suturing device, and wherein the first fusion element bears against the second fusion element by way of a compressive force having a direction that is parallel to the longitudinal axis when the first fusion element is advanced in a distal direction, and further wherein the articulable curved needle is configured to be advanced along a curved path that lays in a plane that is perpendicular to the longitudinal axis of the suturing device.

2. The suturing device of claim 1, wherein the suturing device defines an internal channel through which suture material is advanced toward the curved needle.

3. The suturing device of claim 1, wherein the second fusion element defines a surface that the suture material is compressed against by the first fusion element when fusing the suture.

4. The suturing device of claim 3, further comprising an articulable cutter incorporated into the suturing device to cutaway suture material from the trailing portion of the suture material.

5. The suturing device of claim 1, wherein the articulable curved needle is arcuate in shape.

6. The suturing device of claim 1, wherein advancing the needle is accomplished by rotating the needle about an articulation axis.

7. The suturing device of claim 1, wherein suture material is advanced at the same time that the needle is being advanced.

8. The suturing device of claim 1, wherein the needle is at least partially tubular.

9. A suturing device having an articulable curved needle configured to facilitate advancement of a suture material through tissue, the suturing device defining a longitudinal axis along its length, the suturing device further including a first fusion element and a second fusion element, the first fusion element including a heating element that is displaceable along a direction parallel to the longitudinal axis within the suturing device, and wherein the first fusion element bears against the second fusion element by way of a compressive force having a direction that is parallel to the longitudinal axis when the first fusion element is advanced in a distal direction, and further wherein the articulable curved needle is configured to be advanced along a curved path that lays in a plane that is not parallel to the longitudinal axis of the suturing device.

10. The suturing device of claim 9, wherein the suturing device defines an internal channel through which suture material is advanced toward the curved needle.

11. The suturing device of claim 9, wherein the second fusion element defines a surface that the suture material is compressed against by the first fusion element when fusing the suture.

12. The suturing device of claim 11, further comprising an articulable cutter incorporated into the suturing device to cutaway suture material from the trailing portion of the suture material.

13. The suturing device of claim 9, wherein the articulable curved needle is arcuate in shape.

14. The suturing device of claim 9, wherein advancing the needle is accomplished by rotating the needle about an articulation axis.

15. The suturing device of claim 9, wherein suture material is advanced at the same time that the needle is being advanced.

16. The suturing device of claim 9, wherein the needle is at least partially tubular.

* * * * *